United States Patent
Bille

(10) Patent No.: US 6,610,051 B2
(45) Date of Patent: *Aug. 26, 2003

(54) DEVICE AND METHOD FOR PERFORMING REFRACTIVE SURGERY

(75) Inventor: Josef Bille, Heidelberg (DE)

(73) Assignee: 20/10 Perfect Vision Optische Geraete GmbH, Jeidelberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/976,177

(22) Filed: Oct. 12, 2001

(65) Prior Publication Data
US 2003/0073983 A1 Apr. 17, 2003

(51) Int. Cl.$^7$ ............................................. A61F 02/007
(52) U.S. Cl. ................................. 606/5; 606/10; 606/12
(58) Field of Search ............................. 606/3, 5, 10, 12

(56) References Cited

U.S. PATENT DOCUMENTS

| | | | |
|---|---|---|---|
| 4,309,998 A | 1/1982 | Aron nee Rosa et al. | |
| 4,391,275 A | 7/1983 | Fankhauser et al. | |
| 4,538,608 A | 9/1985 | L'Esperance, Jr. | |
| 4,601,288 A | 7/1986 | Myers | |
| 4,633,866 A | 1/1987 | Peyman | |
| 4,665,913 A | 5/1987 | L'Esperance, Jr. | |
| 4,669,466 A | 6/1987 | L'Esperance | |
| 4,718,418 A | 1/1988 | L'Esperance, Jr. | |
| 4,721,379 A | 1/1988 | L'Esperance | |
| 4,732,148 A | 3/1988 | L'Esperance, Jr. | |
| 4,770,172 A | 9/1988 | L'Esperance, Jr. | |
| 4,907,586 A | 3/1990 | Bille et al. | |
| 4,988,348 A | 1/1991 | Bille | |
| 5,993,438 A | 11/1999 | Juhasz et al. | |
| 6,110,166 A | 8/2000 | Juhasz | |
| 6,451,006 B1 * | 9/2002 | Bille ........................... 606/12 |

* cited by examiner

Primary Examiner—David M. Shay
(74) Attorney, Agent, or Firm—Nydegger & Associates

(57) ABSTRACT

A device and method for altering the refractive properties of the cornea by photodisrupting stromal lamellae involves focusing a laser beam within the stroma. To effectuate tissue alteration with minimal laser energies, the focal point of the laser beam is maintained inside the stromal lamella, rather than on an interface between layers of lamellae. To maintain the focal point inside the lamella, the bubbles that result from the photodisruption are measured using a wavefront detector. When a large bubble is observed, indicating photodisruption on an interface between layers of lamellae, the depth of the focal point, measured from the anterior surface, is adjusted to thereby resume photodisruption inside a lamella. A wavefront detector can be used to track the progress of the photodisruption procedure, providing information that can be used to update the amounts and locations of stromal tissue that must be removed to obtain the desired refractive correction.

22 Claims, 2 Drawing Sheets

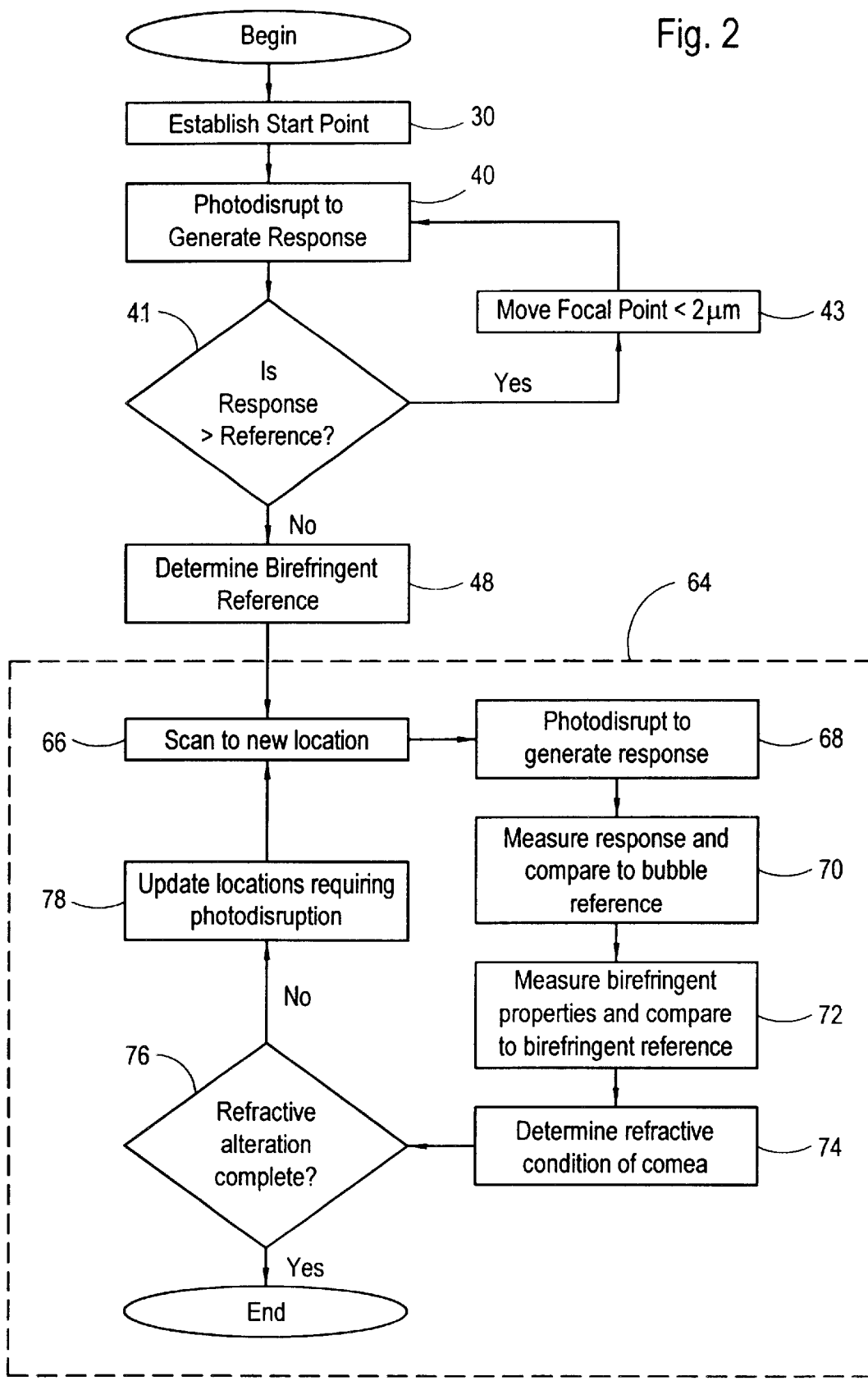

DEVICE AND METHOD FOR PERFORMING REFRACTIVE SURGERY

FIELD OF THE INVENTION

The present invention pertains generally to ophthalmic laser surgery procedures. More particularly, the present invention pertains to laser surgical procedures which are performed to reshape or restructure the cornea of an eye by using photodisruption techniques to remove stromal tissue. The present invention is particularly, but not exclusively, useful as a method and system for focusing laser energy inside a stromal lamella to photodisrupt stromal tissue.

BACKGROUND OF THE INVENTION

It is well known that the refractive properties of the cornea can be altered by the selective removal of corneal tissue. For example, a myopic condition of the eye can be corrected by selectively removing corneal tissue from the central portion of the cornea. Similarly, a hyperoptic condition can be corrected by selectively removing corneal tissue within a peripheral ring surrounding the central portion of the cornea.

A general knowledge of the anatomy of the cornea of an eye is helpful for appreciating the problems that must be confronted during refractive corrections of the cornea. In detail, the cornea comprises various layers of tissue which are structurally distinct. In order, going in a posterior direction from outside the eye toward the inside of the eye, the various layers in a cornea are: an epithelial layer, Bowman's membrane, the stroma, Decimet's membrane, and an endothelial layer. Of these various structures, the stroma is the most extensive and is generally around four hundred microns thick. Additionally, the healing response of the stromal tissue is generally quicker than the other corneal layers. For these reasons, stromal tissue is generally selected for removal in refractive correction procedures.

In detail, the stroma of the eye is comprised of around two hundred identifiable and distinguishable layers of lamellae. Each of these layers of lamellae in the stroma is generally dome-shaped, like the cornea itself, and they each extend across a circular area having a diameter of approximately six millimeters. Unlike the layer that a particular lamella is in, each lamella in the layer extends through a shorter distance of only about one tenth of a millimeter (0.1 mm) to one and one half millimeters (1.5 mm). Thus, each layer includes several lamellae. Importantly, each lamella includes many fibrils which, within the lamella, are substantially parallel to each other. The fibrils in one lamella, however, are not generally parallel to the fibrils in other lamellae. This is so between lamellae in the same layer, as well as between lamellae in different layers. Finally, it is to be noted that, in a direction perpendicular to the layer, each individual lamella is only about two microns thick.

Within the general structure described above, there are at least three important factors concerning the stroma that are of interest insofar as the photodisruption of stromal tissue to effect a refractive change is concerned. The first of these factors is structural, and it is of interest here because there is a significant anisotropy in the stroma. Specifically, the strength of tissue within a lamella is approximately fifty times the strength that is provided by the adhesive tissue that holds the layers of lamellae together. Thus, much less energy is required to separate one layer of lamellae from another layer (i.e. peel them apart), than is required to cut through a lamella. The second factor is somewhat related to the first, and involves the response of the stromal tissue to photodisruption. Specifically, for a given energy level in a photodisruptive laser beam, the bubble that is created by photodisruption in the stronger lamella tissue will be noticeably smaller than a bubble created between layers of lamellae. This is important because the creation of large bubbles tends to cloud the cornea, and thereby reducing the effectiveness of wavefront analysis during the procedure. Additionally, at a given laser energy, much more tissue is photodisrupted when the laser beam is focused inside a lamella than when the laser beam is focused between layers of lamellae.

After the photodisruption of stromal tissue, water resorption occurs, lessening the effect of the photodisruption. For some tissues, up to 80% of the water vapor produced by photodisruption is resorbed. Thus, the present invention recognizes that photodisruption is more effective on some types of stromal tissue than others. It is also preferable to create small bubbles inside the stromal lamellae to effect a refractive change in the cornea by photodisruption. The third factor concerning the stroma is optical, and it is of interest here because there is a change in the refractive index of the stroma between successive layers of lamellae. This is due to differences in the orientations of fibrils in the respective lamella.

Somewhat related to the present invention, a method for finding an interface between layers of lamellae for photodisrupting using a wavefront analyzer and an ellipsometer was disclosed in co-pending U.S. patent application Ser. No. 09/783,665, filed on Feb. 14, 2001 by Bille and entitled "A Method for Separating Lamellae". As such, the contents of co-pending application Ser. No. 09/783,665 are hereby incorporated herein by reference. In co-pending application Ser. No. 09/783,665, a procedure for creating a corneal flap for a LASIK type procedure was presented. Unlike the present invention, the goal in the creation of a corneal flap is to minimize the total amount of tissue that is photodisrupted while establishing a continuous cut of stromal tissue.

In light of the above, it is an object of the present invention to provide a device and method for positioning the focal point of a laser beam inside a stromal lamellae and maintaining the focal point at locations inside the stromal lamellae to photodisrupt stromal tissue and alter the refractive properties of the eye. Another object of the present invention is to provide a method for using a laser beam to photodisrupt relatively large amounts of stromal tissue with a laser beam of relatively low energy. Still another object of the present invention is to provide a method for photodisruption of stromal tissue that avoids the large bubbles and associated clouding that occurs when the laser beam is focused on tissue lying on an interface between layers of lamellae. Another object of the present invention is to provide a device and method for tracking the progress of the photodisruption procedure, providing information that can be used to update the amounts and locations of stromal tissue that must be removed to obtain the desired refractive correction. Yet another object of the present invention is to provide a method for altering the refractive properties of the cornea that is easy to perform and is comparatively cost effective.

SUMMARY OF THE PREFERRED EMBODIMENTS

In accordance with the present invention, a method for altering the refractive properties of the cornea involves photodisrupting tissue at selected locations within the stroma of the cornea. Specifically, each photodisruption location is selected to preferably be inside a stromal lamella rather than at a location between lamellae. By photodisrupting a plurality of stromal lamellae in this manner, the refractive properties of the cornea can be altered at relatively low laser energies and with minimal clouding of the cornea. To photodisrupt a location inside a stromal lamella, the focal point of the laser, and consequently the laser energy, is focused inside a stromal lamella.

For the present invention, a wavefront detector can be used during the photodisruption procedure to track the progress of the corrective procedure. Using the wavefront detector, continuously updated information concerning the refractive properties of the cornea is provided to the surgeon during the course of the procedure. This continually changing information allows the surgeon to select the amounts and locations of stromal tissue that must be subsequently altered to obtain the desired shape for the cornea.

To locate the focal point inside a stromal lamella in accordance with the present invention, the laser beam is initially focused to a start point in the stroma at a depth of approximately one hundred and eighty microns from the anterior surface of the cornea. As contemplated by the present invention, the anterior surface of the cornea can be identified using a wavefront detector. Preferably, the laser beam is set to operate at an energy level that is slightly above the threshold for photodisruption of stromal tissue (i.e. slightly above approximately five microjoules for a ten micron diameter spot size). For example, the initial energy level used for the laser beam may be around six microjoules for a ten micron diameter spot.

Once the start point is located, tissue at the start point is photodisrupted by the laser beam to generate a photodisruptive response (i.e. a bubble is created). The size of this bubble is then measured and compared with a reference value to determine whether the bubble was created inside a lamella or between layers of lamellae. This measurement of the bubble is preferably accomplished with a wavefront detector. If it is determined that the initial bubble was created between layers of lamellae, a subsequent bubble is created at a different point in the stroma. In most cases, this subsequent bubble is created at a smaller depth from the anterior surface of the cornea than the initial bubble. The new bubble is then compared to the reference value to determine whether the new bubble was created inside a lamella. This process is continued until a bubble is created having a bubble size indicating that photodisruption is occurring inside a lamella.

For the purposes of the present invention, the reference value is chosen to correspond to a hypothetical gas bubble in the stroma that, as a result of photodisruption, would have a diameter of approximately fifteen microns. A condition wherein the measured bubble is less than the reference value is indicative that the photodisruption of tissue is occurring in the stronger tissue that is located on the inside of a lamella, rather than at an interface between layers of lamellae. Accordingly, further photodisruption is accomplished by maintaining the initial depth of the laser and moving its focal point to create the desired photodisruption pattern at locations inside the lamella. On the other hand, when the measured bubble is greater than the reference value, the indication is that the focal point is no longer located inside a lamella. Thus, in accordance with the present invention, the depth of the focal point is altered until the subsequent photodisruption occurs inside a lamella (i.e. until a bubble is produced that is smaller than the reference value).

Once a bubble is created indicating that photodisruption has occurred at a location inside a lamella, an ellipsometer can be used to detect a birefringent condition at the location. Specifically, this birefringent condition results from the orientation of fibrils in the lamella. Further, it is known that from layer to layer of lamellae there will be a birefringent change that is manifested as a change in phase of about one half degree. In accordance with the present invention, the detection of the birefringent change can indicate a change from one layer of lamellae to another. Consequently, detection of the birefringent change can be used to establish and maintain a desired focal depth in the stroma.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 2 is a logic flow chart of the sequential steps to be accomplished in accordance with the methods of the present invention;

DESCRIPTION OF THE PREFERRED EMBODIMENT

Figure 1:
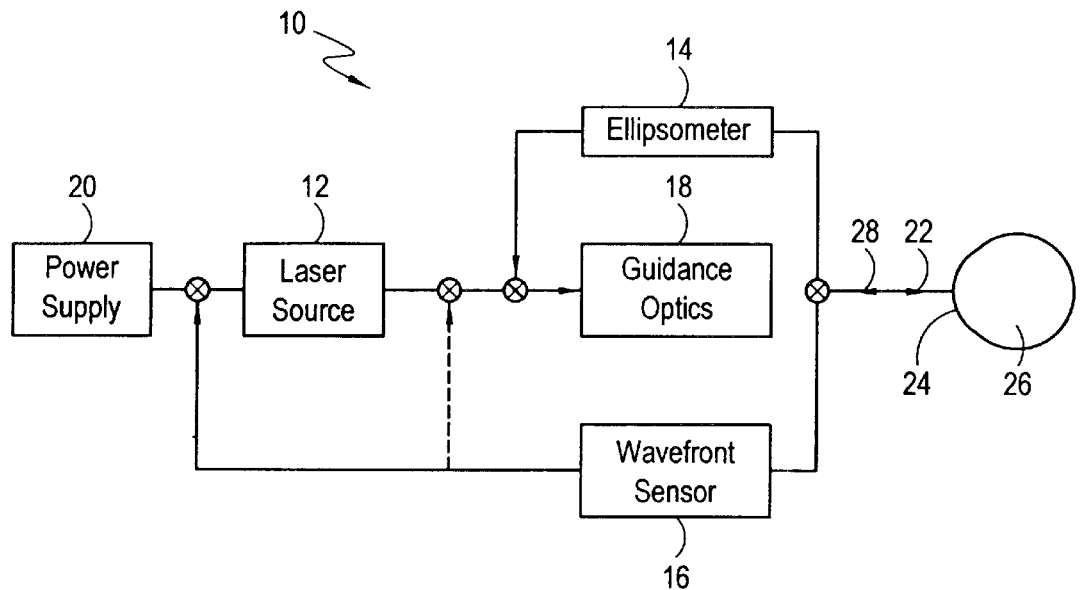
FIG. 1 is a schematic diagram, in a closed-loop feedback control format, showing the operative components of an apparatus that is useful for performing the methods of the present invention.

Referring initially to FIG. 1, an apparatus for use in performing the methods of the present invention is shown schematically in a control loop format and is generally designated 10. As shown, the apparatus 10 includes a laser source 12 which, preferably, is capable of generating a continuous train of ultra-short pulses, with each pulse having a pulse duration of approximately one pico-second. Specifically, it is necessary that each pulse have an energy level that is above the threshold necessary for the photodisruption of stromal tissue. Preferably, for the present invention, a laser source 12 having an energy level of approximately six microjoules per ten micron diameter spot size is provided. The apparatus 10 also includes an ellipsometer 14 that is capable of determining the birefringent properties within stromal tissue. For the purposes of the present invention, an ellipsometer of the type disclosed and claimed in U.S. Pat. No. 5,822,035, which issued to Bille for an invention entitled "Ellipsometer," is suitable. Further, FIG. 1 shows that the apparatus 10 includes a wavefront detector 16, such as a Hartmann-Shack sensor, which is capable of modeling a wavefront. Additionally, the apparatus 10 includes guidance optics 18 that are capable of steering and focusing a laser beam onto predetermined focal points. A power unit 20 is also provided. In combination, these components cooperate with each other to generate a laser beam 22 that is directed to a focal point in the cornea 24 of an eye 26 with a predetermined energy level. Control over this operation, to include the location of the focal point and its energy level, is made possible by using the ellipsometer 14 and the wavefront detector 16 to monitor reflected light 28 as it is reflected from the cornea 24.

Figure 3:
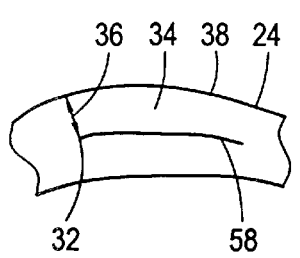
FIG. 3 is a cross sectional view of the cornea of an eye.

Referring now to FIG. 2, it will be seen that in the operation of apparatus 10, the performance of the methods of the present invention begins by establishing a start point (action block 30). In FIG. 3 it will be seen that an actual start point 32 is established in the stroma 34 of cornea 24. Specifically, the start point 32 is established at a distance 36 that is measured from the anterior surface 38 of the cornea 24 in a direction that is substantially perpendicular to the anterior surface 38. As intended for the apparatus 10, the exact location of the anterior surface 38 can be determined using the wavefront detector 16, and the distance 36 can then be arbitrarily chosen to be around about one hundred and eighty microns from the anterior surface 38.

Figure 4:
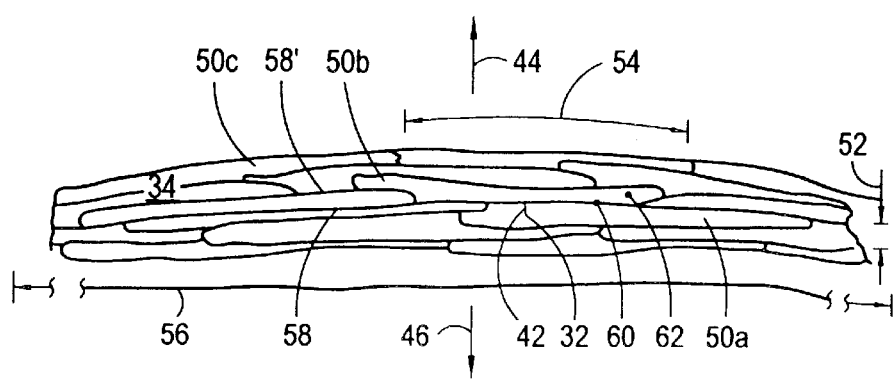
FIG. 4 is a cross sectional view of two exemplary layers of lamellae in the cornea of an eye.

Once a start point 32 has been established in the stroma 34, action block 40 in FIG. 2 indicates that the next step in the methods of the present invention is to photodisrupt tissue at the start point 32 to create a response (i.e. a bubble in the stromal tissue). As indicated by inquiry block 41, this response is then compared with a reference (e.g. 15 $\mu$m). If the response is greater than the reference, action block 43 indicates that the focal point should be moved from the start point 32 through a distance 42 (FIG. 4). This distance 42 will preferably be taken in an anterior direction (indicated by the arrow 44 in FIG. 4) and will, most likely, be less than two microns. It will be appreciated, however, that in some cases this distance 42 may be taken in a posterior direction (indicated by arrow 46 in FIG. 4). In either case, as this movement from the start point 32 is being accomplished, the inquiry block 41 in FIG. 2 indicates that when the response becomes less than the reference, reflected light 28 from cornea 24 can be monitored by the ellipsometer 14 to determine a birefringent reference (action block 48). It happens that this birefringent reference can be determined due to a variation in the orientation of tissue in the stroma 34 and will, perhaps, be best understood by reference to FIG. 4.

In FIG. 4, a portion of the stroma 34 in the cornea 24 of the eye 26 is shown to include a plurality of lamellae 50, of which the lamellae 50a, 50b and 50c are only exemplary. Dimensionally, each of the lamellae 50 in the stroma 34 have a depth 52 that is approximately two microns, and a width 54 that is between approximately one tenth and one and one half millimeters. Thus, the lamellae 50 each have a very thin disk shape. Anatomically, the lamellae 50 lie on top of each other in layers that extend across the cornea 24 through a distance 56 that is approximately nine millimeters. As shown in FIG. 4, the individual lamella 50 overlap to some extent and are somewhat randomly arranged. Nevertheless, they create many interface layers that, in general, are substantially parallel to each other and extend all the way across the cornea 24. The interface 58 shown in FIG. 4 is only exemplary of the many interface layers in the cornea 24.

For the purposes of the present invention, the lamellae 50 and interface layer 58 are important in two aspects. First, the birefringent properties of stromal tissue in the lamellae 50 change at the interface layer 58. Recall, from the disclosure above, this change in birefringent properties is due to changes in the orientation of fibrils (not shown) in the lamellae 50. Thus, by measuring the birefringent properties at different locations within the stroma 34, it can be determined which locations are within the same layer of lamellae 50. Second, the stromal tissue along the interface layer 58 is weaker than stromal tissue inside the lamellae 50. Accordingly, by focusing the laser beam 22 at a location inside a lamella 50, stromal tissue can be effectively photodisrupted at relatively higher rates and at relatively lower energy levels.

It happens that whenever stromal tissue is photodisrupted, a bubble is formed in the stroma 34. For a given type of tissue, the size of the bubble that is formed will be a function of the energy level in the laser beam 22. In this case, the higher the energy level, the larger the bubble. Further, for a given energy level, the size of the bubble that is formed will be a function of the type of tissue photodisrupted. In this case, with the same energy level, the stronger tissue inside a lamella 50 will yield a smaller bubble and the weaker tissue at an interface 58 will yield a larger bubble. With this in mind, consider the photodisruption of locations 60 and 62 shown in FIG. 4 using a laser beam 22 at the same energy level. In accordance with the discussion above, a larger bubble will result at location 60 in weaker tissue at the interface 58 between the lamellae 50a and 50b. On the other hand, a smaller bubble will result at location 62 due to the stronger tissue inside the lamella 50b. Fortunately, as used for the present invention, the respective sizes of the bubbles will serve as photodisruptive responses that can be measured by the wavefront detector 16 using relatively well known wavefront techniques. Accordingly, the photodisruptive response of a bubble can be compared with a reference value to determine whether the bubble resulted from photodisruption of a location 60 on an interface 58 or a location 62 inside a lamella 50.

Returning now to FIG. 2, and in light of the above discussion with reference to FIG. 4, it will be appreciated that the combined functions of inquiry block 41 and action blocks 40 and 43 is to find a location 62 inside a lamella 50. Upon finding a location 62 inside a lamella 50, the ellipsometer 14 (FIG. 1) can be used to establish a birefringent reference (action block 48) for the location 62. Next, once a location 62 inside a lamella 50 is found, the photodisruption of a pattern designed to correct an optical deficiency can be performed. For a typical optical correction, the pattern generally constitutes a volume of stromal tissue having a thickness of five to fifteen (5–15) lamellae. In accordance with the present invention, during the photodisruption of the pattern the focal point is maintained within a single layer of lamella 50. Preferably, the focal point is maintained inside the lamella 50 within a single layer of lamellae. In accordance with the present invention, the refractive condition of the cornea 24 can be periodically measured, and adjustments made to the initial pattern design. These steps are shown in closed loop format by the blocks enclosed by dashed line 64 in FIG. 2.

Referring still to FIG. 2, during photodisruption of the pattern, the guidance optics 18 are used to scan the laser beam 22 to a new location within the pattern (action block 66). Upon photodisruption at the new location (action block 68), the resultant bubble is compared with the reference standard bubble (action block 70). Thus, a determination is made whether the new location is on an interface 58 or inside a lamella 50. For the present invention, the reference standard bubble will correspond to a hypothetical bubble in stromal tissue (not shown) which would have a diameter of approximately fifteen microns. If the resultant bubble in the stroma 34 has a photodisruptive response that is greater than the reference value, it is indicative of the fact that weaker tissue in the interface layer 58 is being photodisrupted. In this case, the focal point should be moved from the start point 32 through a distance 42 (FIG. 4) before photodisrupting the next location within the pattern.

Next, as shown in FIG. 2, the birefringent properties at the new location can be measured (action block 72) using an ellipsometer 14, for comparison to the birefringent reference. This measurement (i.e. action block 72) can be used to determine whether the new location is in the same layer of lamella 50 as the location measured in action block 48. It will happen that locations on two different layers of lamellae 50 will result in a birefringent change on the order of plus or minus one half degree. Importantly, maintaining the focal point within a single layer of lamellae 50 will fix a focal depth for the laser beam 22 that will be an approximate combination of the distances 36 and 42.

Figure 5:
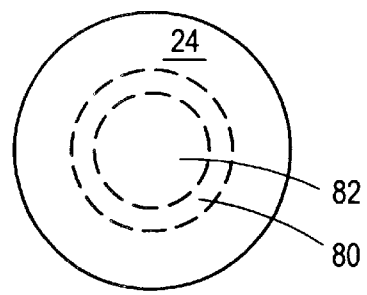
FIG. 5 is a plan view of the cornea of an eye.

Referring still to FIG. 2, for the present invention, the refractive properties of the cornea 24 can be continuously or periodically measured (action block 74). This measurement can be performed with a wavefront detector 16, and is preferably performed on a portion of the cornea that is not being photodisrupted. For example, referring to FIG. 5, during corrections for hyperopia, the photodisruption is often performed in a peripheral ring 80 surrounding the central portion 82 of the cornea 24. In this case, the refractive properties of the central portion 82 of the cornea 24 can be measured with the wavefront detector 16. If further refractive correction is required (inquiry block 76) then the determinations/measurements made in action blocks 70, 72 and 74 can be used to update the locations and amounts of stromal tissue that require photodisruption (i.e. the pattern) to achieve the desired refractive correction (action block 78). With the updated pattern, the laser beam 22 is then scanned to a new location requiring photodisruption (action block 66), and the process enclosed by dashed line 64 is repeated until the desired refractive correction is obtained.

While the particular Method for Performing Refractive Surgery as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An apparatus for photodisrupting stromal lamellae within the cornea of an eye to alter the refractive properties of the cornea, said apparatus comprising:

a means for sequentially focusing a laser beam to focal points at a plurality of locations within the stroma to photodisrupt stromal tissue and create a gas bubble at each said location;

a means for determining whether each said location is inside a stromal lamella; and a means for using said determinations to select a subsequent location for photodisruption that is inside a stromal lamella to alter the refractive properties of the cornea.

2. An apparatus as recited in claim 1 wherein said means for determining whether each location is inside a stromal lamella comprises a wavefront detector.

3. An apparatus as recited in claim 1 further comprising a means for measuring birefringent properties within the stroma, said measuring means for determining whether a subsequent location selected for photodisruption is within a previously photodisrupted layer of lamellae.

4. An apparatus as recited in claim 1 further comprising a means for monitoring the refractive properties of the cornea to determine the extent of photodisruption.

5. An apparatus as recited in claim 4 wherein said monitoring means comprises a wavefront detector.

6. A method for photodisrupting lamellae in the stroma of an eye, said method comprising the steps of:

focusing a laser beam to a focal point at a first location in the stroma to photodisrupt stromal tissue and create a photodisruptive response thereto, said photodisruptive response being indicative of a diameter of a gas bubble created in the stroma during photodisruption;

comparing said photodisruptive response to a reference value; and selecting a second location for photodisruption, said second location being at approximately the same depth from the anterior surface of the cornea as said first location when said photodisruptive response is less than said reference value and said second location being at a different depth from the anterior surface of the cornea than said first location when said photodisruptive response is greater than said reference value.

7. A method as recited in claim 6 wherein said reference value is indicative of a gas bubble in the stroma having a diameter of approximately fifteen microns.

8. A method as recited in claim 6 wherein the depth from the anterior surface of the cornea of said second location is less than the depth from the anterior surface of the cornea of said first location when said photodisruptive response is greater than said reference value.

9. A method as recited in claim 8 wherein said first location is at a depth from the anterior surface of the cornea of approximately one hundred and eighty microns.

10. A method for photodisrupting stromal lamellae within the cornea of an eye to alter the refractive properties of the cornea, said method comprising the steps of:

focusing a laser beam to a focal point in the stroma to photodisrupt stromal tissue and create a gas bubble in response thereto, said gas bubble having a diameter;

comparing said diameter of said gas bubble to a reference value to determine whether said gas bubble is inside a stromal lamella;

using said comparing step to select a subsequent location inside a stromal lamella for photodisruption; and moving said focal point of said laser beam to said selected subsequent location to photodisrupt stromal tissue and create a gas bubble in response thereto to alter the refractive properties of the cornea.

11. A method as recited in claim 1 wherein said comparing step is accomplished by employing a wavefront detector and a processor.

12. A method as recited in claim 1 wherein the energy of said focal point at said focal point is approximately 6 $\mu J$ for a focal point having a 10 $\mu m$ diameter.

13. A method as recited in claim 1 wherein said refractive properties of the cornea are altered to treat a hyperopic condition of the eye.

14. A method as recited in claim 1 wherein said reference value is indicative of a gas bubble in the stroma having a diameter of approximately fifteen microns.

15. A method as recited in claim 1 wherein said focusing step is accomplished in the stroma at a predetermined distance from the anterior surface of the eye.

16. A method as recited in claim 15 wherein the anterior surface of the eye is located using a wavefront detector.

17. A method as recited in claim 15 wherein said predetermined distance is approximately equal to one hundred and eighty microns.

18. A method as recited in claim 1 further comprising the step of repeating said comparing, said using and said moving steps a plurality of times to photodisrupt stromal tissue within the stroma.

19. A method as recited in claim 18 further comprising the step of using a wavefront detector to measure the refractive properties of the cornea to determine said subsequent locations for photodisruption.

20. A method as recited in claim 18 further comprising the step of measuring the birefringent properties of at least two of said locations and using said measurements to select said subsequent location for photodisruption, wherein said subsequent location is selected to be within a layer of stromal lamella.

21. A method as recited in claim 20 wherein said step of measuring the birefringent properties of at least two of said locations is accomplished using an ellipsometer.

22. A method as recited in claim 20 wherein said locations for photodisruption are selected within a peripheral ring surrounding the central portion of the cornea and said wavefront detector is used to measure the refractive properties of the central portion of the cornea to determine subsequent locations for photodisruption.

* * * * *